United States Patent [19]
Burton et al.

[11] Patent Number: 5,792,185
[45] Date of Patent: Aug. 11, 1998

[54] APPARATUS, METHOD, AND SYSTEM WHICH ACCURATELY DISCRIMINATES BETWEEN DEFIBRILLATION ELECTRODES AND HEART MONITORING ELECTRODES

[75] Inventors: David L. Burton; Jonathan N. Andrews, both of McMinnville, Oreg.

[73] Assignee: Hewlett-Packard Company, Palo Alto, Calif.

[21] Appl. No.: 792,968

[22] Filed: Jan. 24, 1997

[51] Int. Cl.⁶ ........................................... A61N 1/04
[52] U.S. Cl. ........................................... 607/2
[58] Field of Search .................. 128/630, 639, 128/641, 696; 607/2, 8, 28

[56] References Cited

U.S. PATENT DOCUMENTS

| | | |
|---|---|---|
| 3,547,108 | 12/1970 | Seiffert et al. . |
| 3,983,407 | 9/1976 | Shott . |
| 4,109,223 | 8/1978 | Tenkman et al. ............... 128/696 |
| 4,355,642 | 10/1982 | Alferness . |
| 4,419,998 | 12/1983 | Heath . |
| 4,810,855 | 3/1989 | Dassi et al. . |
| 4,951,672 | 8/1990 | Buchwald et al. ............... 128/696 |
| 4,955,381 | 9/1990 | Way et al. . |
| 5,002,063 | 3/1991 | Haner ............... 128/696 |
| 5,080,099 | 1/1992 | Way et al. . |
| 5,176,543 | 1/1993 | Brooks . |
| 5,232,383 | 8/1993 | Barnick . |
| 5,295,482 | 3/1994 | Clare et al. . |
| 5,466,256 | 11/1995 | McAdams et al. . |

*Primary Examiner*—William E. Kamm

[57] ABSTRACT

An improved method and system to be utilized with combination defibrillation-heart monitoring equipment and having the ability to distinguish between defibrillation electrodes and monitoring electrodes in an electric circuit electrically connecting combination defibrillation-heart monitoring equipment to a patient. The objects of the method and system are achieved as is now described. At least one resistive element is placed in series with each monitoring electrode. The impedance of the resistive element is chosen such that the impedance is greater than the typical impedance that could be measured between a pair of accurately placed and properly prepared defibrillation electrodes. The resulting series resistive element-monitoring electrode combination is then utilized to distinguish between monitoring electrodes and defibrillation electrodes in an electric circuit electrically connecting combination defibrillation-heart monitoring equipment to a patient. In order to distinguish between the different types of electrodes, the impedance of the circuit formed by electrodes electrically connected to the patient is measured. If the measured impedance is greater than or equal to the impedance of the resistive element placed in series with the monitoring electrodes, then it is determined either that one or more monitoring electrodes are in use or that the defibrillation electrodes are not in good contact with the patient. If it is determined that one or more monitoring electrodes are in use or that the defibrillation electrodes are not in good contact with the patient, the operator is alerted to the determination and appropriate corrective actions are taken before a defibrillation discharge is allowed.

18 Claims, 6 Drawing Sheets

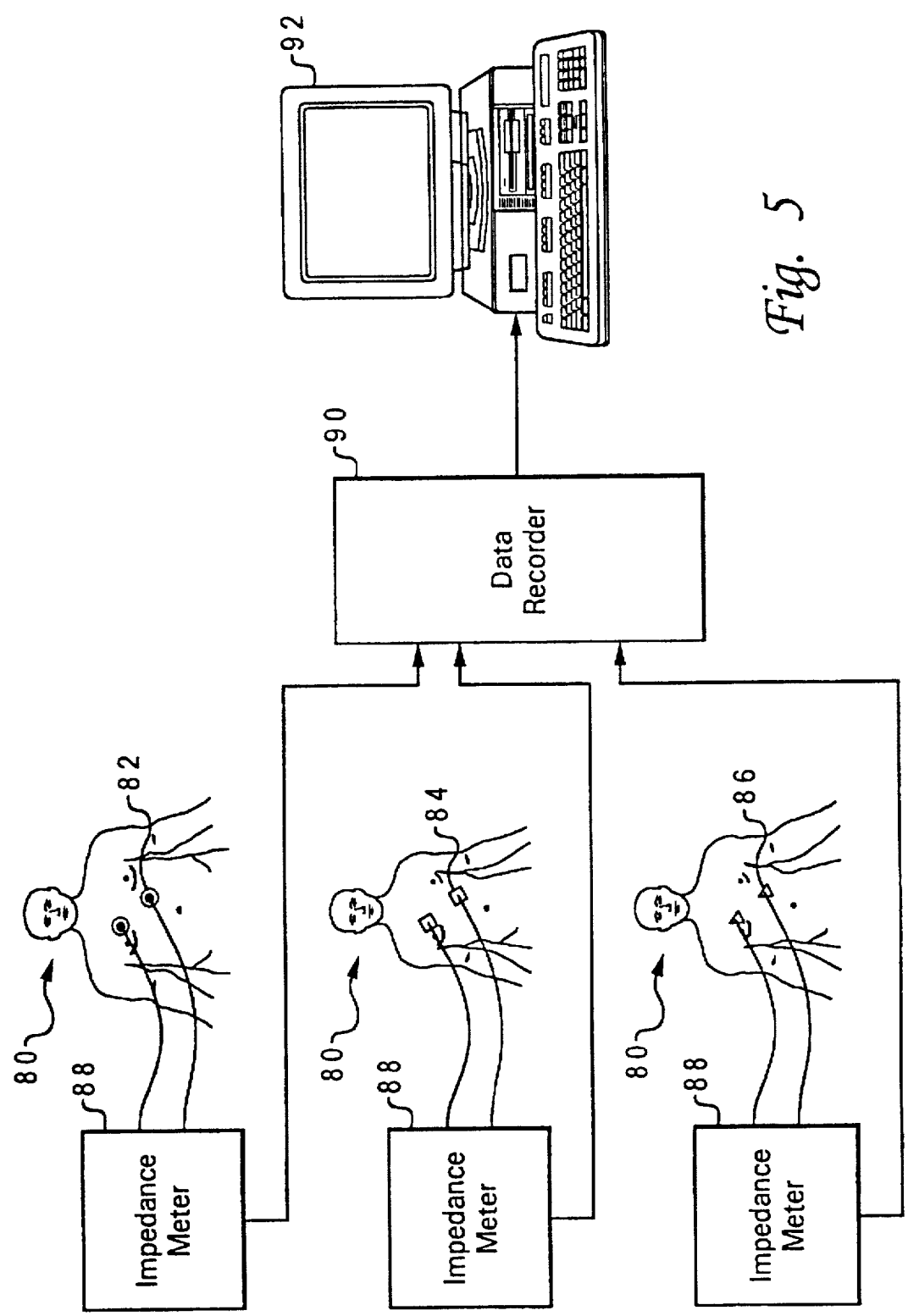

APPARATUS, METHOD, AND SYSTEM WHICH ACCURATELY DISCRIMINATES BETWEEN DEFIBRILLATION ELECTRODES AND HEART MONITORING ELECTRODES

BACKGROUND

1. Technical Field

The present invention relates, in general, to an improved method and system to be utilized with combination defibrillation-heart monitoring equipment. In particular, the present invention relates to an improved method and system to be utilized with combination defibrillation-heart monitoring equipment and having the ability to distinguish between defibrillation electrodes and monitoring electrodes in an electric circuit electrically connecting combination defibrillation-heart monitoring equipment to a patient. Still more particularly, the present invention relates to an improved method and system to be utilized with combination defibrillation-heart monitoring equipment and having the ability to distinguish between defibrillation electrodes and monitoring electrodes in an electric circuit electrically connecting combination defibrillation-heart monitoring equipment to a patient by utilizing resistive elements placed in series with the monitoring electrodes.

2. Description of Related Art

The present invention is directed toward the resolution of problems, discussed below, which exist in the prior art methods and systems utilized with combination defibrillation-heart monitoring equipment. Defibrillation-heart monitoring equipment is equipment which contains both a defibrillation system and a heart monitoring system.

A defibrillation system effects defibrillation. Fibrillation is chaotic and uncoordinated contraction of the ventricular myocardium (heart muscle) arising from spontaneously occurring action potentials. Fibrillation impairs the heart's ability to pump blood. Defibrillation is the causing of the cessation of fibrillation of the ventricular myocardium (heart muscle) by the application of electrical voltage and current to the heart. Defibrillation is achieved by pulsing electrical energy through the heart. The energy is pulsed in such a fashion that virtually the entire heart muscle is simultaneously depolarized, thus extinguishing the spontaneously occurring action potentials. Once this has been done, all portions of the heart muscle repolarize virtually simultaneously and the heart will be in its resting state, and hence will function correctly on the next heartbeat.

Heart monitoring systems effect heart monitoring by detecting the electrochemical activity. Heart monitoring is typically accomplished by the use of an electrocardiogram, which is produced by a device know as the electrocardiograph. During an electrocardiogram (EKG), monitoring electrodes from the electrocardiograph are attached to the body surface. Attaching monitoring electrodes to the body surface allows the voltage changes within the body to be recorded. The EKG is the time log of the voltage changes within the body which were detected by the electrocardiograph. The voltage changes within the body which are recorded are caused by the propagation of an electrochemical "pulse," known as the "action potential" through the heart.

When the action potential propagates within the heart, the net potential change within the body detected by the electrocardiograph is neither very great, nor spread over a very large area (i.e. the energy generated by the action potential is relatively small, generally many orders of magnitude less than the energy discharged by the defibrillation device). In order to detect the net potential change it is known within the art that it is most effective to have monitoring electrodes of very small surface area so as to be able to concentrate the effect of the net potential change within the body that is caused by the propagation of the action potential. Consequently, monitoring electrodes tend to be electrodes with very small surface area. Furthermore, since the detected signal is still generally very weak even when using the very small surface area monitoring electrodes, it is generally necessary to amplify the signal obtained before it can be used.

In contrast to this, it is known within the art that defibrillation electrodes need to pass a large amount of energy in order to defibrillate the heart. Furthermore, it is also known within the art that at any electrode-patient interface heat is created, and that the amount of heat created is directly proportional to the amount of energy passing the interface (the more energy the more heat) and inversely proportional to the surface area of the interface (the smaller the interface the greater the heat). Because of the two foregoing reasons, it is understood within the art that defibrillation electrodes need to have a relatively large surface area so that the defibrillation pulse applied will prove effective and so that the patient is not burned when the defibrillation pulse is applied.

Monitoring electrodes are typically small in order to effectively detect the electrochemical operation of the heart. As set forth above, defibrillation electrodes need to be relatively large in order to effectively defibrillate the heart and avoid electrical burns to the patient. From the foregoing it follows that applying a defibrillation pulse though monitoring electrodes can result in electrical burns and the likelihood that such a discharge will not result in defibrillation. It also follows that utilizing defibrillation electrodes to monitor the heart can result in inaccurate and attenuated signals. It is thus important to use monitoring electrodes when monitoring and defibrillation electrodes when defibrillating.

In order to decrease the likelihood that monitoring electrodes will be connected when the defibrillation pulse is applied and vice versa, many companies have implemented combination defibrillation-heart monitoring equipment which uses the same cable set to either (1) connect the defibrillation electrodes to the defibrillation-heart monitoring equipment when defibrillation is needed, or (2) connect the monitoring electrodes to the defibrillation-heart monitoring equipment when monitoring is needed. The cables are such that only one set of electrodes can be connected to the defibrillation-heart monitoring equipment at one time, and different type cable adapters are used to either connect the cable set to defibrillation electrodes or monitoring electrodes. Using the same cable set with different type cable adapters is intended to decrease the likelihood that the monitoring electrodes will be connected when the defibrillation pulse is applied and vice versa.

Generally, the cables will be connected to monitoring electrodes and the combination defibrillation-heart monitoring equipment will be monitoring a patient's heart function. When the need for defibrillation arises, the cables are manually disconnected from the monitoring electrodes and then manually reconnected to the defibrillation electrodes. A problem that arises from this arrangement is how to ensure that one does not leave the cables connected to one or more monitoring electrodes when a defibrillation pulse is applied, and thus inadvertently discharge a defibrillation pulse through one or more monitoring electrodes. Or, conversely, leave the cables connected to one or more defibrillation electrodes after the defibrillation pulse is applied, and thus inadvertently attempt to monitor using defibrillation electrodes.

The prior art solution to this problem has been either to rely upon the user to correctly connect the electrodes, or to monitor the impedance between the connected electrodes in order to determine which electrodes are in use. These solutions have at least two deficiencies in that (1) during an emergency situation, humans are often prone to make mistakes, and (2) sensing the impedance between the electrodes can be an unreliable indicator. One reason that sensing the impedance between the electrodes can be unreliable is that impedance measurement varies from person to person in that differing skin types and body builds often yield different impedance measurements, even when the same electrode pair is used. Another reason that sensing the impedance between the electrodes can be unreliable is that accurate impedance measurement requires that the electrodes be both correctly placed and supplied with a sufficiently good electrolytic connection between the electrodes and the body. For example, in the absence of correct electrode placement and good electrolytic connection, the impedance sensed can yield incorrect information as to the type of electrodes in use. Specifically, correctly prepared and placed defibrillation electrodes should have relatively low measured impedance, but such electrodes, when incorrectly prepared and placed, can yield relatively high impedance measurements (since if the charge carriers are unable to communicate one will effectively have an open circuit). Conversely, the small monitoring electrodes, when correctly placed and prepared, will yield relatively high impedance measurements. One can see that the problem can become quite complex when the combinations are permutated (i.e. inadvertently utilizing a defibrillation electrode with a monitoring electrode, with the possibility that either type of electrode could be incorrectly prepared and placed).

At present, it is not possible to discern with a high degree of confidence whether defibrillation or monitoring electrodes are being used in an electric circuit connecting defibrillation-heart monitoring equipment to a particular patient. The present invention solves this problem and others deriving from it by introducing an innovative method and system which utilize an unprecedented series resistive element-monitoring electrode combination.

Thus, it is apparent that a need exists for a method and system which will accurately determine whether defibrillation or one or more monitoring electrodes are operationally connected to combination defibrillation-heart monitoring equipment, and take appropriate actions in response to the type of electrodes detected.

SUMMARY OF THE INVENTION

It is therefore one object of the present invention to provide an improved method and system to be utilized with combination defibrillation-heart monitoring equipment.

It is another object of the present invention to provide an improved method and system to be utilized with combination defibrillation-heart monitoring equipment and having the ability to distinguish between defibrillation electrodes and monitoring electrodes in an electric circuit electrically connecting combination defibrillation-heart monitoring equipment to a patient.

It is yet another object of the invention to provide an improved method and system to be utilized with combination defibrillation-heart monitoring equipment and having the ability to distinguish between defibrillation electrodes and monitoring electrodes in the electric circuit electrically connecting combination defibrillation-heart monitoring equipment to a patient by utilizing resistive elements placed in series with the monitoring electrodes.

The foregoing objects are achieved as is now described. At least one resistive element is placed in series with each monitoring electrode. The impedance of the resistive element is chosen such that the impedance is greater than the typical impedance that could be measured between a pair of accurately placed and properly prepared defibrillation electrodes. The resulting series resistive element-monitoring electrode combination is then utilized to distinguish between monitoring electrodes and defibrillation electrodes in an electric circuit electrically connecting combination defibrillation-heart monitoring equipment to a patient. In order to distinguish between the different types of electrodes, the impedance of the circuit formed by electrodes electrically connected to the patient is measured. If the measured impedance is greater than or equal to the impedance of the resistive element placed in series with each monitoring electrode, then it is determined either that one or more monitoring electrodes are in use or that the defibrillation electrodes are not in good contact with the patient. If it is determined that one or more monitoring electrodes are in use or that the defibrillation electrodes are not in good contact with the patient, the operator is alerted to the determination and appropriate corrective actions are taken before a defibrillation discharge is allowed.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

FIG. 5 illustrates a high-level schematic view of a system for choosing the at least one series resistive element so that the present invention will function correctly.

DETAILED DESCRIPTION OF PREFERRED EMBODIMENT

Figure 1:
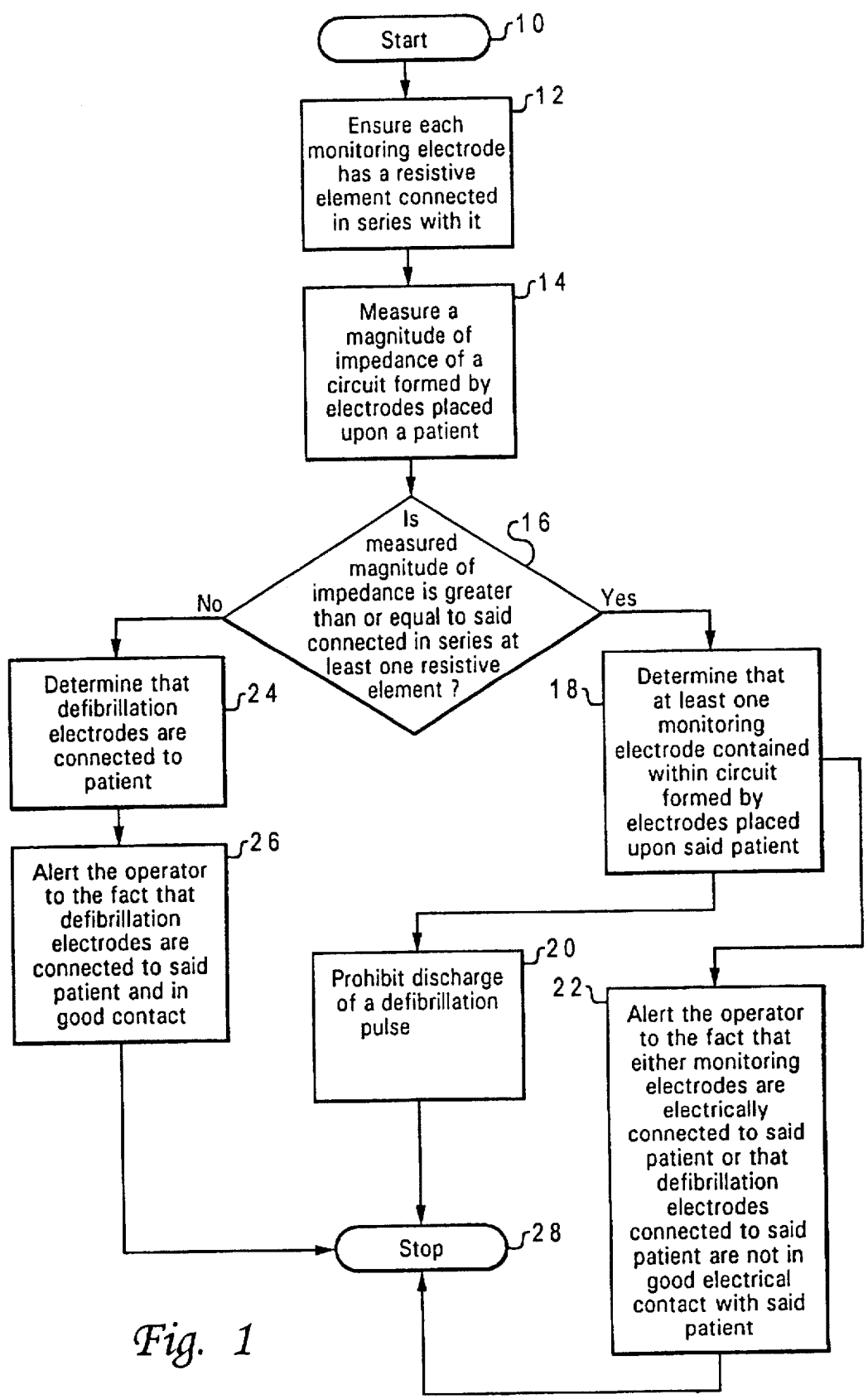
FIG. 1 is a high-level logic flowchart depicting the method and process of the present invention.

With reference now to the figures and in particular with reference now to FIG. 1, it can be seen that FIG. 1 is a high-level logic flowchart depicting the method and process of the present invention. Method step 10 illustrates the start of the process. Method step 12 depicts the ensurance that each monitoring electrode to be used with combination defibrillation-heart monitoring equipment will have connected in series with it a resistive element. The resistive element of method step 12 to be connected in series is chosen in the fashion shown in FIG. 2 and is such that the resistive element's impedance exceeds the impedance that one would expect to see in any likely circuit formed by correctly prepared and placed defibrillation electrodes electrically connected to a patient.

Method step 14 illustrates the measurement of the impedance of the circuit formed by electrodes of unknown type (with said type possibly being either defibrillation or monitoring electrodes) electrically connected to a specific patient. Method step 16 compares the measured impedance of the circuit formed by electrodes of unknown type electrically connected to a specific patient to the impedance of the series connected resistive element of method step 12. If the measured impedance of the circuit formed by electrodes of unknown type electrically connected to a specific patient is greater than or equal to the impedance of the series connected resistive element of method step 12, then method step 18 shows that it is determined that at least one of the electrodes in the circuit path formed by the electrodes electrically connected to a patient is a monitoring electrode, and the method proceeds to any one or both of method steps 20 and 22. If the measured impedance of the circuit formed by electrodes of unknown type electrically connected to a specific patient is less than the impedance of the series connected resistive element of method step 12, then method step 24 shows that it is determined that none of the electrodes in the circuit path formed by the electrodes electrically connected to a patient is a monitoring electrode, and the method proceeds to method step 26.

Method step 20 shows the prohibition of the discharge of a defibrillation pulse since it has been determined that there is likely a monitoring electrode in the path. Method step 22 depicts the alerting of the operator of the combination defibrillation-heart monitoring equipment to the fact that either one or more monitoring electrodes are in the circuit path formed by the electrodes or the possibility that the defibrillation electrodes are not well electrically connected (if the defibrillation electrodes are not well electrically connected the impedance could appear to be quite large). After either or both of method steps 20 and 22 are traversed the process stops at method step 28.

Method step 26 shows the alerting of the operator of the combination defibrillation-heart monitoring equipment to the fact that the defibrillation electrodes are connected to the patient and that the defibrillation electrodes have good electrical contact. Method step 28 shows the stopping of the process.

Figure 2:
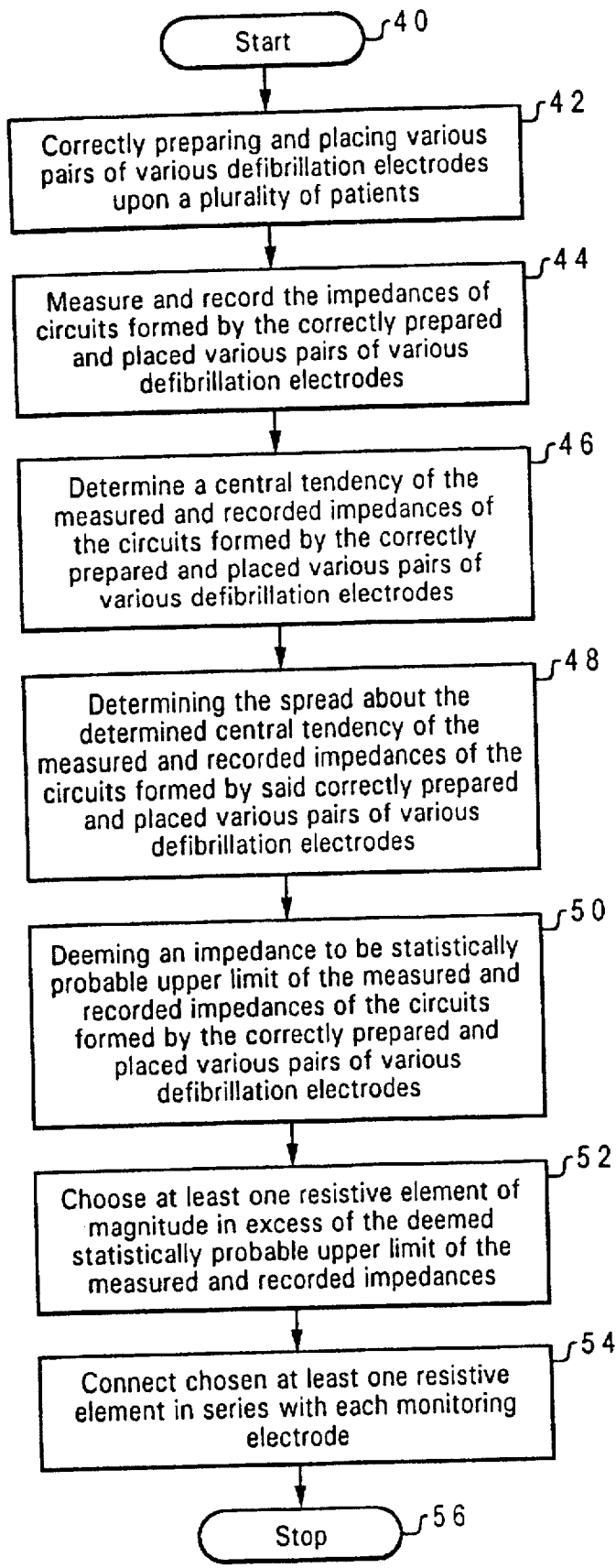
FIG. 2 is a high-level logic flowchart depicting a method for selecting the appropriate resistances for use within the present invention.

Referring now to FIG. 2, it can be seen that FIG. 2 is a high-level logic flowchart depicting a method for selecting the appropriate resistances for use within the present invention. Method step 40 shows the start of the process. Method step 42 depicts correctly preparing and placing various pairs (pairs doesn't necessarily mean there are only two electrodes being prepared and placed, but rather means that the impedance of a number of electrodes dispersed over a patient is measured between two electrical nodes; that is, there could be three electrodes on a body, and the pair would be a pair of electrical nodes, with the first electrical node being that formed by two of the electrodes taken together and the second electrical node being the remaining electrode which will form a second electrical node) of different defibrillation electrodes (different shapes, sizes, and compositions) which could reasonably be expected to be used with the combination defibrillation-heart monitoring equipment. This exercise is repeated with a plurality of patients (fat, thin, young, etc.) so that a wide range of impedance values may be obtained.

Method step 44 shows the measuring and recording of the impedances obtained in method step 42. Method step 46 shows the determination of a central tendency (e.g., the mean or median) of the measured and recorded impedances obtained in method step 42. Method step 48 shows the determination of the spread (e.g., variance or standard deviation) of the data about the central tendency determined in method step 46. Method step 50 depicts the deeming of an impedance to be the statistically probable upper limit of the impedances measured and recorded in method step 42 (e.g., it could be deemed that an impedance value beyond three standard deviations is statistically improbable).

Method step 52 shows the choosing of the at least one resistive element to be placed in series with each monitoring electrode as in method step 12. Shown is that impedance of the chosen at least one resistive element is in excess of the deemed upper limit of the impedance which was discussed in relation to method step 52. Method step 54 depicts that the at least one resistive element chosen in method step 52 is to be connected in series with each monitoring electrode. Method step 56 illustrates the stopping of the process.

Figure 3B:
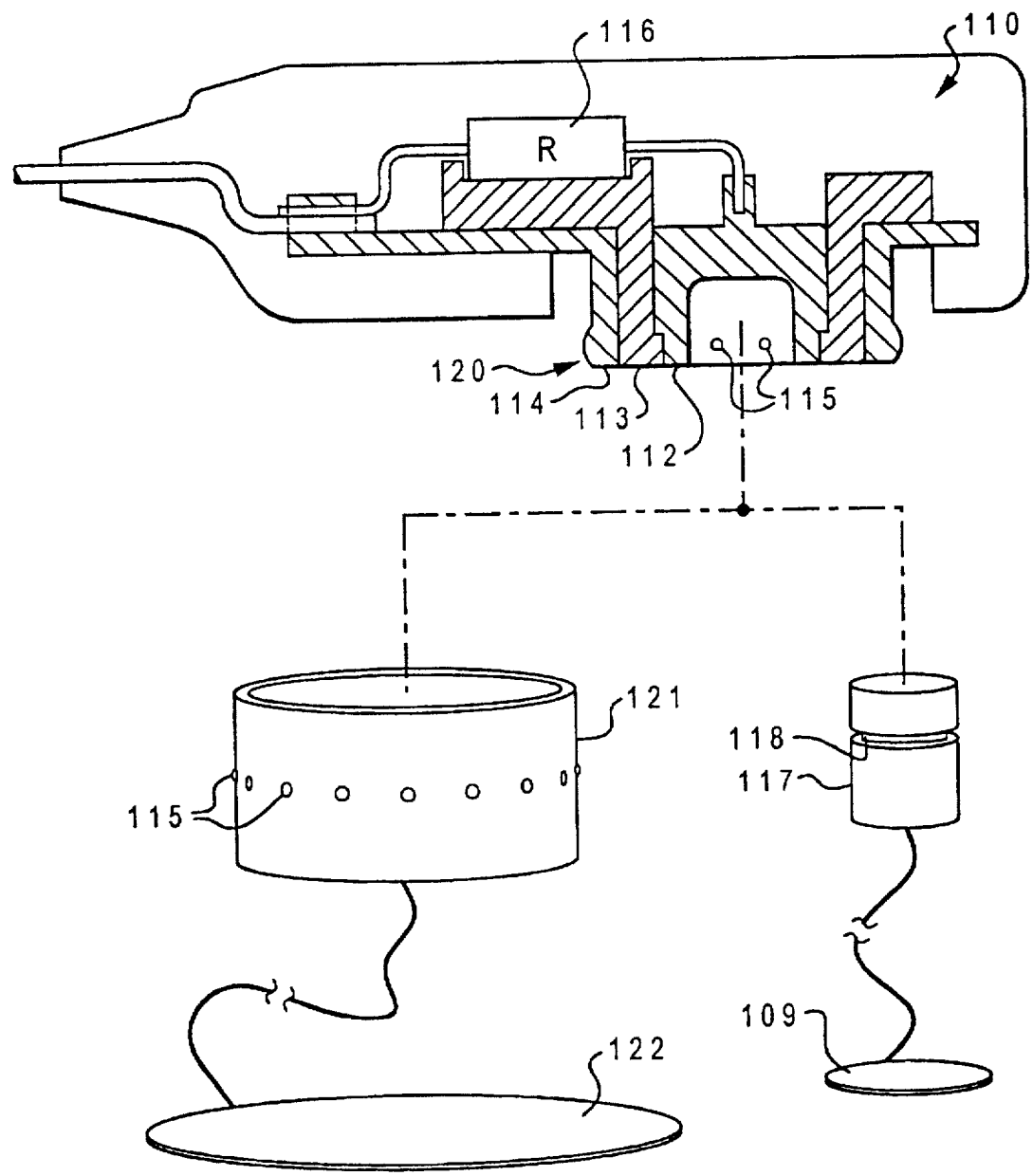
FIGS. 3A, 3B, and 3C illustrate two different embodiments of the series resistor-electrode combinations utilized in the present invention.
Figure 3A:
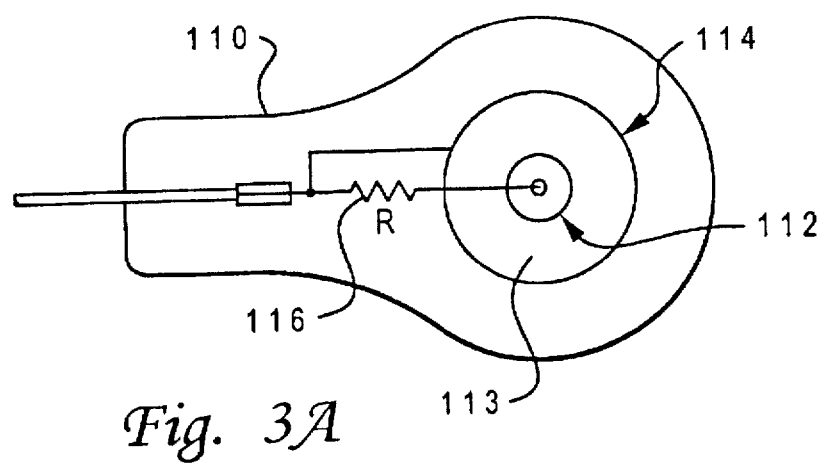
Figure 3C:
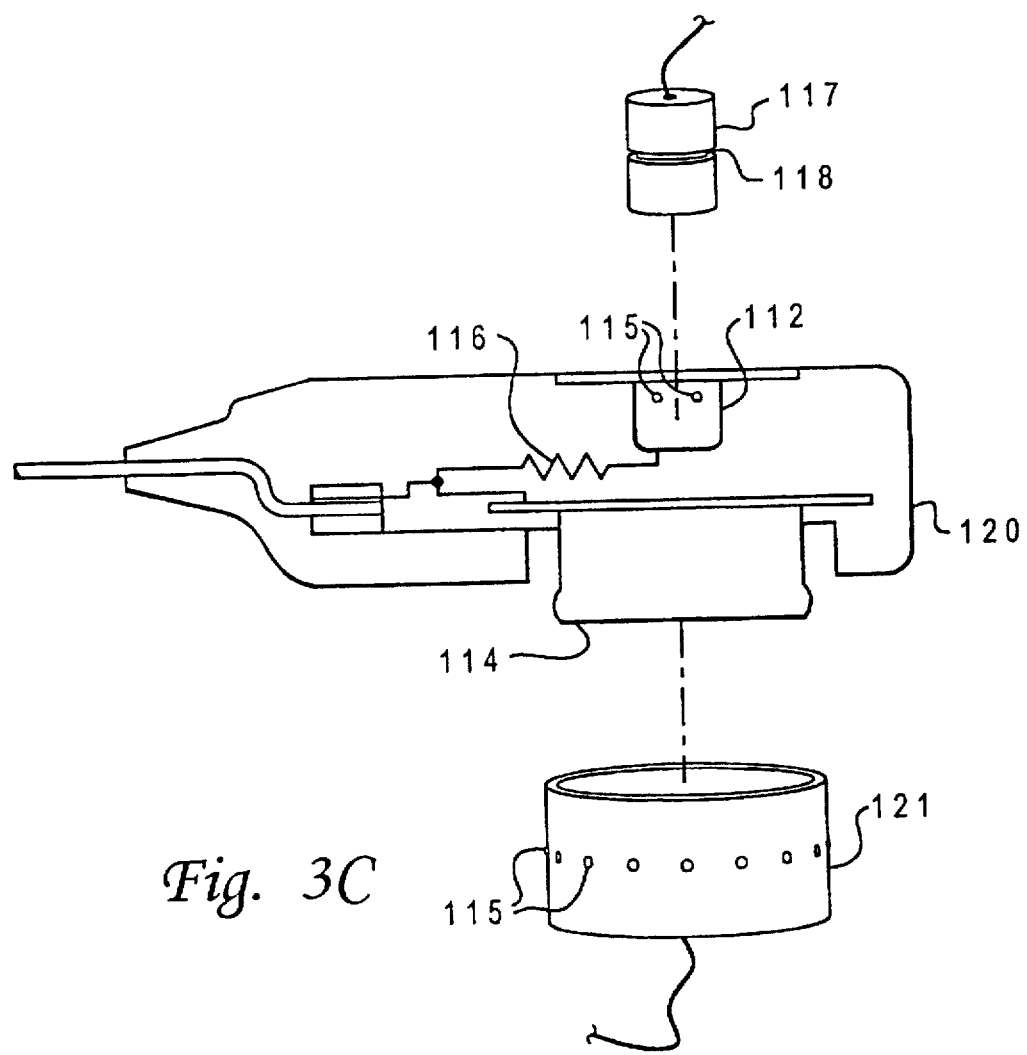

Refer now to FIGS. 3A, 3B, and 3C which illustrate two different embodiments of the series resistor-monitoring electrode snap connectors utilized to achieve the series resistor-monitoring electrode combination of the present invention. One embodiment is shown in FIG. 3A to be a molded casing 110 with a female monitoring electrode snap connector 112, much smaller than and contained within a larger male defibrillation electrode snap connector 114, with female monitoring electrode snap connector 112 and the larger male defibrillation electrode snap connector 114 being separated by an electrically insulating material 113, such as glass, in such a fashion that no current can flow between female monitoring electrode snap connector 112 and male defibrillation electrode snap connector 114. Shown is the at least one resistive element 116, of chosen impedance larger than that likely to be encountered when using correctly prepared and placed defibrillation electrodes, connected in series with female monitoring electrode snap connector 112.

FIG. 3B shows a cutaway expanded view of the series resistive element-monitoring electrode connectors of FIG. 3A. Shown is female monitoring electrode snap connector 112 wherein is also shown the arrangement of a row of spring loaded ball bearing fasteners 115 arranged on the inner surface of female monitoring electrode snap connector 112 such that when male monitoring electrode snap connector 117 is inserted into female monitoring electrode snap connector 112 the ball bearings interface snugly (snap into place) within circumferential channel 118 cut about male monitoring electrode snap connector 117, such that a firm electrical connection is established and maintained between said connectors. Male monitoring electrode snap connector 117 is shown series connected to monitoring electrode 109, so that when the firm electrical connection is established between male monitoring electrode snap connector 117 and female monitoring electrode snap connector 112 such connection achieves the series connection of the at least one resistive element 116 with monitoring electrode 109. Also shown is electrically insulating material 113 which separates female monitoring electrode snap connector 112 from male defibrillation electrode snap connector 114. Male defibrillation electrode snap connector 114 is shown with a raised lip 120, but alternatively could be presented with a circumferential channel 118, which is fashioned such that spring loaded ball bearing fasteners 115 of female defibrillation electrode snap connector 121 will snap into place behind raised lip 120 such that a firm electrical connection is established and maintained between male defibrillation electrode snap connector 114 and female defibrillation electrode snap connector 121. Female defibrillation electrode snap connector 121 is shown series connected to defibrillation electrode 122, so that the when the firm electrical connection is established between male defibrillation electrode snap connector 114 and female defibrillation electrode snap connector 121, such connection achieves the series connection with defibrillation electrode 122. In addition to the foregoing, it will be understood by those skilled in the art that the functionality of the row of spring loaded ball bearing fasteners 115 described in this application could also be obtained by the use of either a spring loaded clip or a circular spring clip. Furthermore, in the preferred embodiment of the female monitoring electrode snap connector 112, a spring loaded clip is used in lieu of the row of spring loaded ball bearing fasteners 115, and in the preferred embodiment of the female defibrillation electrode snap connector 121 a circular spring clip is used in lieu of the row of spring loaded ball bearing fasteners 115.

FIG. 3C illustrates a second embodiment of the series resistor-monitoring electrode snap connector utilized to achieve the series resistor-monitoring electrode combination of the present invention. Shown in the figure is a different molded casing 120. In this embodiment, male defibrillation electrode snap connector 114 and female monitor electrode snap connector 112 are placed in diametrically opposed positions as shown in the figure; however, at least one resistive element 116, of chosen impedance larger than that likely to be encountered connected in when using correctly prepared and placed defibrillation electrodes, is still in series with the monitoring electrodes, as is shown. Male defibrillation electrode snap connector 114 and female monitor electrode snap connector 112 interface with their opposites (male monitoring electrode snap connector 117 and female defibrillation electrode snap connector 121) to form series connections as has been described in relation to FIG. 3B and as is incorporated by reference here.

Figure 4:
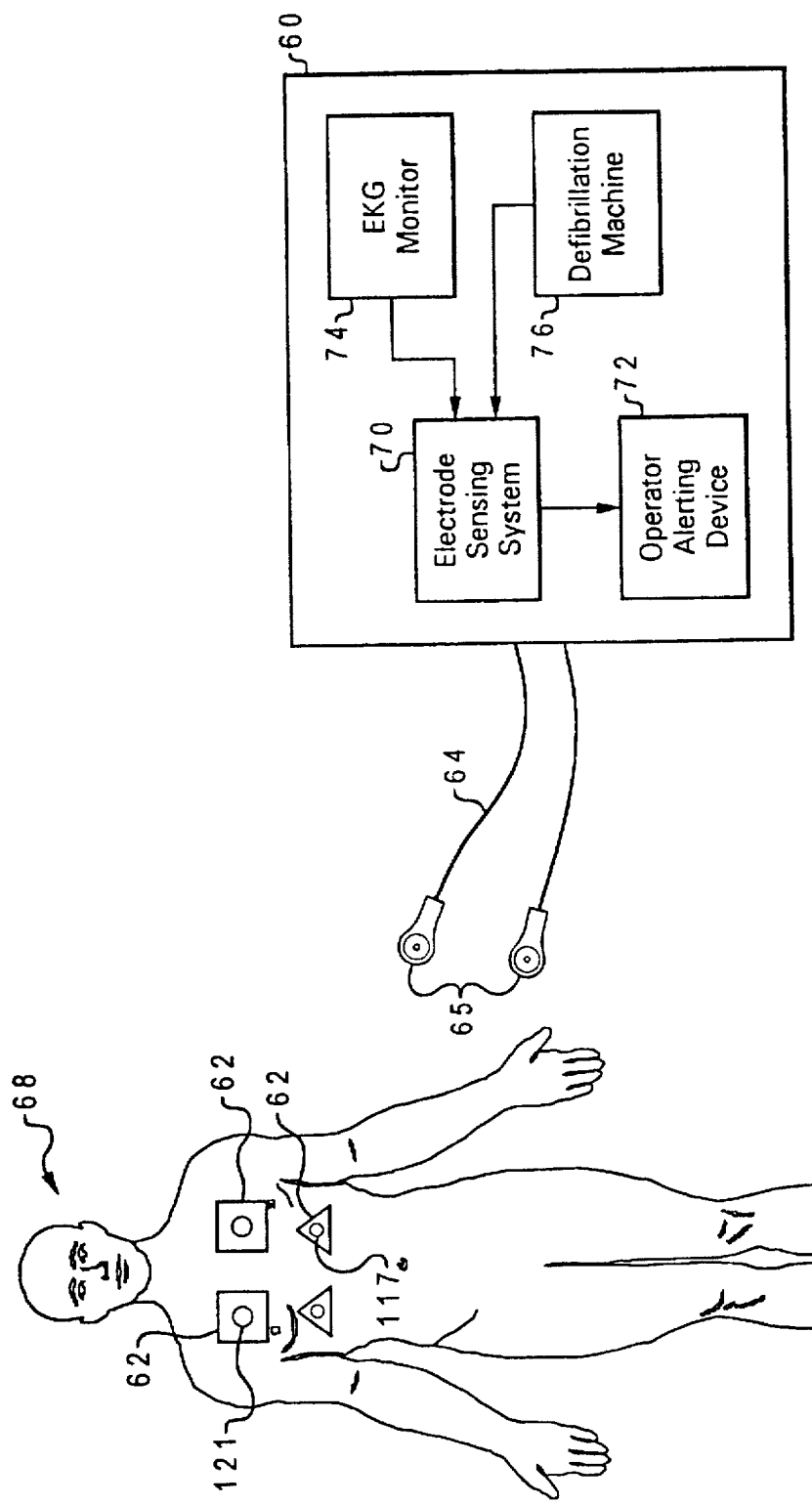
FIG. 4 depicts a high-level schematic view of a system for implementing the present invention.

Referring now to FIG. 4, there is depicted a high level schematic view of a system for implementing the present invention. Shown is combination defibrillation-heart monitoring equipment 60 which can be electrically connected via conducting cables 64, which in the preferred embodiment has electrode connectors 65 of the type shown in FIGS. 3A, 3B, or 3C, by which conducting cables 64 electrically connect to various pads 62 wherein reside various female defibrillation electrode snap connectors 121 and various male monitoring electrode snap connectors 117 which serve as the electrical connections to both defibrillation 122 and monitoring electrodes 109 which are on the under-surfaces (and hence not shown in FIG. 4) of various pads 62 which interface with the body of patient 68.

As is apparent upon a review of FIG. 4, it is not possible to discern easily which type of electrodes conducting cables 64 are connected to since the features of the electrodes are hidden from view and are on the surface of various pads 62 which interface with the body of patient 68. Electrode sensing system 70 contains impedance sensing, computing (e.g., a microprocessor), switching, and memory circuitry (e.g., DRAM) as appropriate and essentially accomplishes all the functions of method steps 14, 16, 18, 20, and 24 (e.g., the microprocessor is programmed to use the impedance sensing circuitry and carry out these method steps) and thus controls the interface between patient 68 and EKG MONITOR 74 and Defibrillation machine 76. Once electrode sensing system 70, which is interfaced with operator alerting device 72, has determined the type of electrodes present, it passes the information to operator alerting device 72. Operator alerting device 72 contains alerting circuitry including but not limited to visual displays and audio alarms, and uses the information received from electrode sensing system 70 in order to accomplish the functions of method steps 26 and 22.

With reference now to FIG. 5, there is illustrated a high-level schematic view of a system for choosing the at least one series resistive element so that the present invention will function correctly. Shown are a number of patients 80 to whom different types of correctly prepared and placed defibrillation electrodes 82, 84, 86 have been attached. The intent of the illustration is to show that many different types of patients (fat, average, muscular, male, female) are tested with many different types of defibrillation electrodes affixed to them. Shown are impedance meters 88 which are used to test the impedance offered by the circuit formed by the defibrillation electrodes in contact with the patients 80. In the preferred embodiment the impedance is measured at a frequency of 33 kHz.

Also shown in FIG. 5 is data recorder 90 which records the impedances sensed by impedance meters 88. Data recorder 90 transfers the recorded measured impedances to computing device 92 (which could be a personal computer, microcomputer, etc.). At the completion of data gathering, computing device 92 calculates the central tendency for the measured impedances and the spread about same as discussed in method steps 46–48. Subsequent to this, computing device 92 specifies a value of impedance which, on the basis of the calculated central tendency and spread it deems to be the highest impedance likely to be encountered in correctly prepared and placed defibrillation electrodes. An impedance value is then chosen which is in excess of the highest impedance likely to be encountered as was specified by computing device 92, and the impedance of the resistance elements connected in series with each monitoring electrode to be used with combination defibrillation-heart monitoring equipment is always to be greater than or equal to the highest impedance likely to be encountered. In the preferred embodiment, the impedance likely to be encountered with defibrillation electrodes was found to be from 100–400 ohms, and it was determined that it was statistically improbable that the impedance would exceed 500 ohms. Accordingly, the resistor chosen to be placed in series with the monitoring electrode is to be of 500 ohms or higher.

While an illustrative embodiment has been particularly shown and described, it will be understood by those skilled in the art that various changes in form and detail may be made therein without departing from the spirit and scope of the illustrative embodiment.

What is claimed is:

1. A series resistive element-monitoring electrode combination that can be clearly differentiated from at least one defibrillation electrode, said series resistive element-monitoring electrode combination being comprised of:

a monitoring electrode;

at least one resistive element having an impedance in excess of an impedance of a circuit formed by defibrillation electrodes correctly prepared and placed upon a patient; and said at least one resistive element electrically connected in series with said monitoring electrode such that said at least one resistive element electrically connected in series with said monitoring electrode is utilized to clearly differentiate said series resistive element-monitoring electrode combination from said at least one defibrillation electrode.

2. The series resistive element-monitoring electrode combination of claim 1 wherein said at least one resistive element has a measured impedance at least equal to 500 ohms when excited by a 33 kilohertz frequency signal.

3. The series resistive element-monitoring electrode combination of claim 1 wherein said at least one resistive element electrically connected in series with said monitoring electrode further comprises:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a first end of said at least one resistive element being electrically connected in series with said female monitoring electrode snap connector and a second end of said at least one resistive element capable of being operably connected to at least one terminal of a combination defibrillation-heart monitoring equipment;

said monitoring electrode being electrically connected in series with said male monitoring electrode snap connector; and said male monitoring electrode snap connector being inserted within said female monitoring electrode snap connector such that said ball bearings engage said notch channel and hold said male monitoring electrode snap connector and said female monitoring electrode snap connector together such that an electrical connection is maintained whereby said at least one resistive element is electrically connected in series with said monitoring electrode.

4. The series resistive element-monitoring electrode combination of claim 1 wherein said at least one resistive element electrically connected in series with said monitoring electrode further comprises:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a female defibrillation electrode snap connector of cylindrical shape having both an inner and outer surface and having ball bearings springably mounted circularly within said inner surface of said female defibrillation electrode snap connector and wherein said female defibrillation electrode snap connector is formed so as to receive a male defibrillation electrode snap connector of cylindrical shape having both an inner and an outer surface and having a notch channel cut circumferentially into said outer surface of said male defibrillation electrode snap connector, said notch channel of appropriate size to receive said springably mounted ball bearings and such that when said male defibrillation electrode snap connector is inserted within said female defibrillation electrode snap connector said ball bearings engage said notch channel and hold said male and female defibrillation electrode snap connectors together such that an electrical connection is maintained;

a male defibrillation electrode snap connector of cylindrical shape having both an inner and an outer surface and having a notch channel cut circumferentially into said outer surface of said female defibrillation electrode snap connector, said notch channel of appropriate size to receive said springably mounted ball bearings and such that when male defibrillation electrode snap connector is inserted within said female defibrillation electrode snap connector said ball bearings engage said notch channel and hold said male and female defibrillation electrode snap connectors together such that an electrical connection is maintained;

a first end of said at least one resistive element being electrically connected in series with said female monitoring electrode snap connector and a second end of said at least one resistive element capable of being operably connected to at least one terminal of a combination defibrillation-heart monitoring equipment;

said monitoring electrode being electrically connected in series with said male monitor electrode snap connector;

said male defibrillation electrode snap connector capable of being operably connected to at least one terminal of a combination defibrillation-heart monitoring equipment;

said female defibrillation electrode snap connector electrically connected in series with a defibrillation electrode;

said outer surface of said female monitoring electrode shape being concentrically contained within said inner surface of said male defibrillation electrode with said outer surface of said female monitoring electrode and said inner surface of said male defibrillation electrode being separated by an insulating material which prohibits the flow of electric current between said female monitoring electrode and said male defibrillation electrode whereby said female monitoring electrode and said male defibrillation electrode form an integral unit; and said integral unit comprised of said female monitoring electrode concentrically contained within said male defibrillation electrode utilized such that said male monitoring electrode snap connector is inserted within said female monitoring electrode snap connector such that said ball bearings engage said notch channel and hold said female and male monitoring electrode snap connectors together such that an electrical connection is maintained whereby at said least one resistive element is electrically connected in series with said monitoring electrode and whereby said female defibrillation electrode is blocked from connecting with said male defibrillation electrode.

5. The series resistive element-monitoring electrode combination of claim 1 wherein said at least one resistive element electrically connected in series with said monitoring electrode further comprises:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a first end said at least one resistive element being electrically connected in series with said male monitoring electrode snap connector and a second end of said at least one resistive element being electrically connected in series with said monitoring electrode;

said female monitoring electrode being capable of being operably connected to at least one terminal of a combination defibrillation-heart monitoring equipment; and said male monitoring electrode snap connector being inserted within said female monitoring electrode snap connector such that said ball bearings engage said notch channel and hold said male monitoring electrode snap connector and said female monitoring electrode snap connector together such that an electrical connection is maintained whereby said at least one resistive element is electrically connected in series with said monitoring electrode.

6. The series resistive element-monitoring electrode combination of claim 1 wherein said at least one resistive element electrically connected in series with said monitoring electrode further comprises:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a first end said at least one resistive element being electrically connected in series with said male monitoring electrode snap connector and a second end of said at least one resistive element being electrically connected in series with said monitoring electrode;

said female monitoring electrode snap connector being capable of being operably connected to at least one terminal of a combination defibrillation-heart monitoring equipment;

a female defibrillation electrode snap connector of cylindrical shape having both an inner and outer surface and having ball bearings springably mounted circularly within said inner surface of said female defibrillation electrode snap connector and wherein said female defibrillation electrode snap connector is formed so as to receive a male defibrillation electrode snap connector of cylindrical shape having both an inner and an outer surface and having a notch channel cut circumferentially into said outer surface of said male defibrillation electrode snap connector, said notch channel of appropriate size to receive said springably mounted ball bearings and such that when said male defibrillation electrode snap connector is inserted within said female defibrillation electrode snap connector said ball bearings engage said notch channel and hold said male and female defibrillation electrode snap connectors together such that an electrical connection is maintained;

a male defibrillation electrode snap connector of cylindrical shape having both an inner and an outer surface and having a notch channel cut circumferentially into said outer surface of said male defibrillation electrode snap connector, said notch channel of appropriate size to receive said springably mounted ball bearings and such that when said male defibrillation electrode snap connector is inserted within said female defibrillation electrode snap connector said ball bearings engage said notch channel and hold said male and female defibrillation electrode snap connectors together such that an electrical connection is maintained;

said male defibrillation electrode snap connector capable of being operably connected to at least one terminal of a combination defibrillation-heart monitoring equipment;

said female defibrillation electrode snap connector electrically connected in series with a defibrillation electrode;

said outer surface of said female monitoring electrode snap connector being concentrically contained within said inner surface of said male defibrillation electrode with said outer surface of said female monitoring electrode and said inner surface of said male defibrillation electrode being separated by an insulating material which prohibits the flow of electric current between said female monitoring electrode and said male defibrillation electrode whereby said female monitoring electrode and said male defibrillation electrode form an integral unit; and said integral unit comprised of said female monitoring electrode concentrically contained within said male defibrillation electrode utilized such that said male monitoring electrode snap connector is inserted within said female monitoring electrode snap connector such that said ball bearings engage said notch channel and hold said male monitoring electrode snap connector and said female monitoring electrode snap connector together such that an electrical connection is maintained whereby at said least one resistive element is electrically connected in series with said monitoring electrode and whereby said female defibrillation electrode is blocked from connecting with said male defibrillation electrode.

7. A system, to be utilized with combination defibrillation-heart monitoring equipment, for distinguishing between defibrillation electrodes and monitoring electrodes in an electric circuit operatively coupling combination defibrillation-heart monitoring equipment to a patient, said system comprising:

at least one monitoring electrode;

at least one resistive element having an impedance in excess of an impedance of a circuit formed by defibrillation electrodes correctly prepared and placed upon a patient;

at least one series resistive element-monitoring electrode combination comprised of said at least one resistive element electrically connected in series with said at least one monitoring electrode;

at least one defibrillation electrode;

means for measuring an impedance of a circuit formed by electrodes placed upon a patient when said circuit formed by electrodes placed upon said patient is operatively coupled to combination defibrillation-heart monitoring equipment; and means, responsive to said means for measuring, for distinguishing between defibrillation electrodes and monitoring electrodes by determining whether said measured impedance of said circuit formed by electrodes placed upon said patient is at least equal to an impedance of said electrically connected in series at least one resistive element of said at least one series resistive element-monitoring electrode combination.

8. The system of claim 7, further comprising means, responsive to said means for distinguishing, for prohibiting the discharge of a defibrillation pulse if said measured impedance of said circuit formed by electrodes placed upon said patient is at least equal to said impedance of said electrically connected in series at least one resistive element of said at least one series resistive element-monitoring electrode combination.

9. The system of claim 7, further comprising means, responsive to said means for distinguishing, for alerting the operator of said combination defibrillation-heart monitoring equipment to the fact that either monitoring electrodes are connected to said patient or that defibrillation electrodes connected to said patient are not in good electrical contact with said patient if said measured impedance of said circuit formed by electrodes placed upon said patient is at least equal to said impedance of said electrically connected in series at least one resistive element of said at least one series resistive element-monitoring electrode combination.

10. A method, to be utilized with combination defibrillation-heart monitoring equipment, for distinguishing between defibrillation electrodes and monitoring electrodes in an electric circuit operatively coupling combination defibrillation-heart monitoring equipment to a patient, said method comprising the steps of:

providing at least one monitoring electrode;

providing at least one resistive element having an impedance in excess of an impedance of a circuit formed by defibrillation electrodes correctly prepared and placed upon a patient;

creating series resistive element-monitoring electrode combinations by connecting at least one of said at least one resistive element electrically connected in series with said at least one monitoring electrode;

providing at least one defibrillation electrode;

measuring an impedance of a circuit formed by electrodes placed upon a patient when said circuit formed by electrodes placed upon said patient is operatively coupled to combination defibrillation-heart monitoring equipment; and in response to said measuring step, distinguishing between defibrillation electrodes and monitoring electrodes by determining whether said measured impedance of said circuit formed by electrodes placed upon said patient is at least equal to an impedance of said electrically connected in series at least one resistive element of said at least one series resistive element-monitoring electrode combination.

11. The method of claim 10, further comprising the step of, in response to said distinguishing step, prohibiting the discharge of a defibrillation pulse if said measured impedance of said circuit formed by electrodes placed upon said patient is at least equal to said impedance of said electrically connected in series at least one resistive element of said at least one series resistive element-monitoring electrode combination.

12. The method of claim 10, further comprising the step of, in response to said distinguishing step, alerting the operator of said combination defibrillation-heart monitoring equipment to the fact that either monitoring electrodes are connected to said patient or that defibrillation electrodes connected to said patient are not in good electrical contact with said patient if said measured impedance of said circuit formed by electrodes placed upon said patient is at least equal to said impedance of said electrically connected in series at least one resistive element of said at least one series resistive element-monitoring electrode combination.

13. A series resistive element-monitoring electrode snap connector combination utilized to form a series resistive element-monitoring electrode combination that can be clearly differentiated from at least one defibrillation electrode, said series resistive element-monitoring electrode snap connector combination being comprised of:

a monitoring electrode snap connector;

at least one resistive element having an impedance in excess of an impedance of a circuit formed by defibrillation electrodes correctly prepared and placed upon a patient; and said at least one resistive element electrically connected in series with said monitoring electrode snap connector such that said at least one resistive element electrically connected in series with said monitoring electrode is utilized to clearly differentiate said series resistive element-monitoring electrode combination from said at least one defibrillation electrode.

14. The series resistive element-monitoring electrode combination of claim 13 wherein said at least one resistive element has a measured impedance at least equal to 500 ohms when excited by a 33 kilohertz frequency signal.

15. The series resistive element-monitoring electrode snap connector combination of claim 13 further comprising:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive a male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained; and a first end of said at least one resistive element being electrically connected in series with said male monitoring electrode snap connector and a second end capable of being operably connected to at least one terminal of a combination defibrillation-heart monitoring equipment.

16. The series resistive element-monitoring electrode snap connector combination of claim 15 further comprising:

a male defibrillation electrode snap connector of cylindrical shape having both an inner and an outer surface and having a notch channel cut circumferentially into said outer surface of said male defibrillation electrode snap connector, said notch channel of appropriate size to receive springably mounted ball bearings from a female defibrillation electrode snap connector of cylindrical shape having both an inner and outer surface and having ball bearings springably mounted circularly within said inner surface of said female defibrillation electrode snap connector and wherein said female defibrillation electrode snap connector is formed so as to receive said male defibrillation electrode snap connector and such that when said male defibrillation electrode snap connector is inserted within said female defibrillation electrode snap connector said ball bearings engage said notch channel and hold said male and female defibrillation electrode snap connectors together such that an electrical connection is maintained; and said outer surface of said female monitoring electrode snap connector being concentrically contained within said inner surface of said male defibrillation electrode with said outer surface of said female monitoring electrode and said inner surface of said male defibrillation electrode being separated by an insulating material which prohibits the flow of electric current between said female monitoring electrode and said male defibrillation electrode whereby said female monitoring electrode and said male defibrillation electrode form an integral unit.

17. The series resistive element-monitoring electrode snap connector combination of claim 13 further comprising:

a male monitoring electrode snap connector of cylindrical shape having both an inner and an outer surface and having a notch channel cut circumferentially into said outer surface of said male monitoring electrode snap connector, said notch channel of appropriate size to receive springably mounted ball bearings from a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive said male monitoring electrode snap connector and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained; and a first end said at least one resistive element being electrically connected in series with said male monitoring electrode snap connector and a second end of said at least one resistive element being electrically connected in series with said monitoring electrode.

18. The series resistive element-monitoring electrode snap connector combination of claim 17 further comprising:

a female monitoring electrode snap connector of cylindrical shape having both an inner and an outer surface and having ball bearings springably mounted circularly within said inner surface of said female monitoring electrode snap connector and wherein said female monitoring electrode snap connector is formed so as to receive said male monitoring electrode snap connector of cylindrical shape having both an inner and an outer surface and having a notch channel cut circumferentially into said outer surface of said male monitoring electrode snap connector, said notch channel of appropriate size to receive said springably mounted ball bearings and such that when said male monitoring electrode snap connector is inserted within said female monitoring electrode snap connector said ball bearings engage said notch channel and hold said male monitoring electrode snap connector and said female monitoring electrode snap connector together such that an electrical connection is maintained;

a male defibrillation electrode snap connector of cylindrical shape having both an inner and an outer surface and having a notch channel cut circumferentially into said outer surface of said male defibrillation electrode snap connector, said notch channel of appropriate size to receive springably mounted ball bearings from a female defibrillation electrode snap connector of cylindrical shape having both an inner and outer surface and having ball bearings springably mounted circularly within said inner surface of said female defibrillation electrode snap connector and wherein said female defibrillation electrode snap connector is formed so as to receive said male defibrillation electrode snap connector and such that when said male defibrillation electrode snap connector is inserted within said female defibrillation electrode snap connector said ball bearings engage said notch channel and hold said male and female defibrillation electrode snap connectors together such that an electrical connection is maintained; and said outer surface of said female monitoring electrode snap connector being concentrically contained within said inner surface of said male defibrillation electrode with said outer surface of said female monitoring electrode and said inner surface of said male defibrillation electrode being separated by an insulating material which prohibits the flow of electric current between said female monitoring electrode and said male defibrillation electrode whereby said female monitoring electrode and said male defibrillation electrode form an integral unit.

* * * * *